United States Patent
Liu

(10) Patent No.: US 8,959,741 B2
(45) Date of Patent: *Feb. 24, 2015

(54) METHOD OF FABRICATING A POROUS ORTHOPEDIC IMPLANT

(71) Applicant: Bio2 Technologies, Inc., Woburn, MA (US)

(72) Inventor: James Jenq Liu, Mason, OH (US)

(73) Assignee: Bio2 Technologies, Inc., Woburn, MA (US)

( * ) Notice: Subject to any disclaimer, the term of this patent is extended or adjusted under 35 U.S.C. 154(b) by 45 days.

This patent is subject to a terminal disclaimer.

(21) Appl. No.: 13/908,627

(22) Filed: Jun. 3, 2013

(65) Prior Publication Data

US 2014/0175693 A1    Jun. 26, 2014

Related U.S. Application Data

(63) Continuation of application No. 13/228,886, filed on Sep. 9, 2011, now Pat. No. 8,468,673.

(60) Provisional application No. 61/381,666, filed on Sep. 10, 2010.

(51) Int. Cl.
| | |
|---|---|
| *B21D 53/00* | (2006.01) |
| *A61F 2/28* | (2006.01) |
| *B29C 44/12* | (2006.01) |
| *A61L 33/02* | (2006.01) |
| *A61L 27/06* | (2006.01) |
| *A61L 27/56* | (2006.01) |

(52) U.S. Cl.
CPC ............... *A61L 33/027* (2013.01); *A61L 27/06* (2013.01); *A61L 27/56* (2013.01); *A61L 2430/02* (2013.01)

USPC ..... 29/419.1; 29/527.1; 623/23.51; 623/23.55; 264/45.3

(58) Field of Classification Search
USPC ........ 29/407.01, 407.05, 419.1, 527.1, 527.2; 623/23.51, 23.53, 23.55, 23.61; 264/44, 45.3
See application file for complete search history.

(56) References Cited

U.S. PATENT DOCUMENTS

| | | |
|---|---|---|
| 3,906,550 A | 9/1975 | Rostoker et al. |
| 3,992,725 A | 11/1976 | Homsy |
| 4,479,271 A | 10/1984 | Bolesky et al. |
| 4,503,157 A | 3/1985 | Hatahira |
| 4,534,936 A | 8/1985 | Carlstrom et al. |

(Continued)

FOREIGN PATENT DOCUMENTS

WO    WO-2008/000049    1/2008

OTHER PUBLICATIONS

Levine, Brett "A New Era in Porous Metals: Applications in Orthopaedics", *Advanced Engineering Materials*, 10, No. 9,(2008).

(Continued)

*Primary Examiner* — Jermie Cozart

(57) ABSTRACT

A tissue scaffold fabricated from bioinert fiber forms a rigid three-dimensional porous matrix having a bioinert composition. Porosity in the form of interconnected pore space is provided by the space between the bioinert fiber in the porous matrix. Strength of the porous matrix is provided by bioinert fiber fused and bonded into the rigid three-dimensional matrix having a specific pore size and pore size distribution. The tissue scaffold supports tissue in-growth to provide osteoconductivity as a tissue scaffold, used for the repair of damaged and/or diseased bone tissue.

12 Claims, 7 Drawing Sheets

(56) References Cited

U.S. PATENT DOCUMENTS

| | | | |
|---|---|---|---|
| 4,693,721 A | 9/1987 | Ducheyne | |
| 4,978,358 A | 12/1990 | Bobyn | |
| 5,030,233 A | 7/1991 | Ducheyne | |
| 5,104,410 A | 4/1992 | Chowdhary | |
| 5,323,954 A | 6/1994 | Shetty et al. | |
| 5,397,365 A | 3/1995 | Trentacosta | |
| 5,629,186 A | 5/1997 | Yasukawa et al. | |
| 5,879,398 A | 3/1999 | Swarts et al. | |
| 5,926,685 A | 7/1999 | Krebs et al. | |
| 5,961,554 A | 10/1999 | Janson et al. | |
| 6,187,329 B1 | 2/2001 | Agrawal et al. | |
| 6,451,059 B1 | 9/2002 | Janas et al. | |
| 6,679,913 B2 | 1/2004 | Homsy | |
| 6,846,327 B2 | 1/2005 | Khandkar et al. | |
| 6,945,448 B2 | 9/2005 | Medlin et al. | |
| 7,241,486 B2 | 7/2007 | Pirhonen | |
| 7,419,679 B2 | 9/2008 | Kuboki | |
| 7,458,991 B2 | 12/2008 | Wang et al. | |
| 7,537,664 B2 | 5/2009 | O'Neill et al. | |
| 8,468,673 B2 * | 6/2013 | Liu | 29/419.1 |
| 2002/0120336 A1 | 8/2002 | Santilli | |
| 2002/0160033 A1 | 10/2002 | Caplice et al. | |
| 2003/0220696 A1 | 11/2003 | Levine et al. | |
| 2006/0073181 A1 | 4/2006 | Kuboki | |
| 2006/0100716 A1 | 5/2006 | Lerf | |
| 2007/0152364 A1 | 7/2007 | Zuberi et al. | |
| 2007/0162151 A1 | 7/2007 | Chang et al. | |
| 2007/0196230 A1 | 8/2007 | Hamman et al. | |
| 2008/0124766 A1 | 5/2008 | Kuboki et al. | |
| 2008/0188942 A1 | 8/2008 | Brown et al. | |
| 2008/0213611 A1 | 9/2008 | Asgari | |
| 2008/0249638 A1 | 10/2008 | Asgari | |
| 2008/0318044 A1 | 12/2008 | Tian et al. | |
| 2009/0035511 A1 | 2/2009 | Liu et al. | |
| 2009/0157194 A1 | 6/2009 | Shikinami | |
| 2009/0166580 A1 | 7/2009 | Tanaka et al. | |
| 2010/0331986 A1 | 12/2010 | Shikinami | |
| 2011/0144764 A1 | 6/2011 | Bagga et al. | |

OTHER PUBLICATIONS

Bobyn, J.D. et al., "Characteristics of bone ingrowth and interface mechanics of a new porous tantalum biomaterial", *Journal of Bone & Joint Surgery (Br)*, vol. 81-B, No. 5,(1999),907-914.

Ridzwan, M.I.Z. et al., "Problem of Stress Shielding and Improvement to the Hip Implant Designs: A Review", *J. Med. Sci.*, 7 (3),(2007),460-467.

Lopez-Heredia, M.A. et al., "Bone growth in rapid prototyped porous titanium implants", *Journal of Biomedical Materials Research Part A*, 85A,(2008),664-673.

Li, Jia Ping et al., "Bone ingrowth in porous titanium implants produced by 3D fiber deposition", *Biomaterials*, 28,(2007),2810-2820.

Huddleston, Ji et al., "A Comparative Study of Bone Ingrowth into Porous Metallic Materials", *56th Annual Meeting of the Orthopaedic Research Society*, Paper No. 154,(2010).

Wazen, Rima M., et al., "Initial evaluation of bone ingrowth into a novel porous titanium coating", *Journal of Biomedical Materials Research B*, Appl Biomater 94B, Issue 1,(2010),64-72.

Otsuki, Bungo et al., "Pore throat size and connectivity determine bone and tissue ingrowth into porous implants", *Biomaterials*, 27,(2006),5892-5900.

Ryan, Garrett E., et al., "Porous titanium scaffolds fabricated using a rapid prototyping and powder metallurgy technique", *Biomaterials*, 29,(2008),3625-3635.

Assad, M. et al., "Porous Titanium-Nickel for Intervertebral Fusion in a Sheep Model: Part 2. Surface Analysis and Nickel Release Assessment", *J Biomed Mater Res Part B*, Appl Biomater 64B,(2003), 121-129.

Prymak, Oleg et al., "Morphological characterization and in vitro biocompatibility of a porous nickel-titanium alloy", *Biomaterials*, 26,(2005),5801-5807.

Sevilla, P. et al., "Comparison of the mechanical properties between tantalum and nickel-titanium foams implant materials for bone ingrowth applications", *Journal of Alloys and Compounds*, 439,(2007),67-73.

Rahaman, M.N. et al., "Fabrication of dense thin sheets of g-TiAl by hot isostatic pressing of tape-cast monotapes", *Materials Science & Engineering A*, 360,(2003), 169-175.

Zhao, Desheng et al., "Mechanical verification of soft-tissue attachment on bioactive glasses and titanium implants", *Acta Biomaterialia*, 4,(2008),1118-1122.

Shimko, Daniel et al., "Effect of Porosity on the Fluid Flow Characteristics and Mechanical Properties of Tantalum Scaffolds", *J Biomed Mater Res Part B*, Appl. Biomater 73B,(2005),315-324.

Ponader, Sabine et al., "In vivo performance of selective electron beam-melted Ti-6Al-4V structures", *J Biomed Mater Res*, 92A,(2010),56-62.

Krishna, B. Vamsi et al., "Low stiffness porous Ti structures for load-bearing implants", *Acta Biomaterialia*, 3,(2007),997-1006.

Zou, Chunming et al., "Preparation, microstructure and mechanical properties of porous titanium sintered by Ti fibres", *J Mater Sci, Mater Med* 19,(2008),401-405.

Tiainen, Hanna et al., "Ultra-porous titanium oxide scaffold with high compressive strength", *J Mater Sci, Mater Med* 21,(2010),2783-2792.

Niinomi, M. "Fatigue characteristics of metallic biomaterials", *International Journal of Fatigue*, 29,(2007),992-1000.

\* cited by examiner

METHOD OF FABRICATING A POROUS ORTHOPEDIC IMPLANT

CROSS REFERENCE TO RELATED APPLICATIONS

This application is a continuation of U.S. patent application Ser. No. 13/228,886 filed Sep. 9, 2011, entitled "Method of Fabricating a Porous Orthopedic Implant" which claims the benefit of Provisional Application No. 61/381,666 filed Sep. 10, 2010, entitled "Devices and Methods for Tissue Engineering," the contents of each are incorporated herein by reference.

FIELD OF THE INVENTION

The present invention relates generally to the field of porous medical implants. More specifically, the invention relates to a bioinert fibrous implant having osteostimulative properties in applications of in vivo environments.

BACKGROUND OF THE INVENTION

Prosthetic devices are often required for repairing defects in bone tissue in surgical and orthopedic procedures. Prostheses are increasingly required for the replacement or repair of diseased or deteriorated bone tissue in an aging population and to enhance the body's own mechanism to produce rapid healing of musculoskeletal injuries resulting from severe trauma or degenerative disease.

Autografting and allografting procedures have been developed for the repair of bone defects. In autografting procedures, bone grafts are harvested from a donor site in the patient, for example from the iliac crest, to implant at the repair site, in order to promote regeneration of bone tissue. However, autografting procedures are particularly invasive, causing risk of infection and unnecessary pain and discomfort at the harvest site. In allografting procedures, bone grafts are used from a donor of the same species but the use of these materials can raise the risk of infection, disease transmission, and immune reactions, as well as religious objections. Accordingly, synthetic materials and methods for implanting synthetic materials have been sought as an alternative to autografting and allografting.

Synthetic prosthetic devices for the repair of defects in bone tissue have been developed in an attempt to provide a material with the mechanical properties of natural bone materials, while promoting bone tissue growth to provide a durable and permanent repair. Knowledge of the structure and biomechanical properties of bone, and an understanding of the bone healing process provides guidance on desired properties and characteristics of an ideal synthetic prosthetic device for bone repair. These characteristics include, but are not limited to: osteostimulation and/or osteoconductivity to promote bone tissue in-growth into the device as the wound heals; and load bearing or weight sharing to support the repair site yet exercise the tissue as the wound heals to promote a durable repair.

Materials developed to date have been successful in attaining at least some of the desired characteristics, but nearly all materials compromise at least some aspect of the bio-mechanical requirements of an ideal hard tissue scaffold.

BRIEF SUMMARY OF THE INVENTION

The present invention meets the objectives of an effective synthetic bone prosthetic for the repair of bone defects by providing a scaffold that is osteostimulative, and load bearing with mechanical properties that match the living tissue at the implant site. The present invention provides a tissue scaffold of bioinert metal fiber with specific pore morphology and sintered to form a rigid three dimensional porous matrix. The porous matrix has interconnected pore space with a pore size distribution in the range of about 50 µm to about 600 µm with porosity between 40% and 85% to provide osteoconductivity once implanted in bone tissue. Embodiments of the present invention include pore space having a multi-modal pore size distribution.

Methods of fabricating a synthetic bone prosthesis according to the present invention are also provided that include mixing bioinert fiber with volatile components including a pore former, and a liquid to provide a plastically formable batch, and kneading the formable batch to distribute the metal fiber into a substantially homogeneous mass of intertangled and overlapping metal fiber. The formable batch is dried, heated to remove the volatile components and to form bonds between the intertangled and overlapping bioinert fiber.

These and other features of the present invention will become apparent from a reading of the following descriptions and may be realized by means of the instrumentalities and combinations particularly pointed out in the appended claims.

BRIEF DESCRIPTION OF THE SEVERAL VIEWS OF THE DRAWING

The foregoing and other objects, features, and advantages of the invention will be apparent from the following detailed description of the several embodiments of the invention, as illustrated in the accompanying drawings in which like reference characters refer to the same parts throughout the different views. The drawings are not necessarily to scale, with emphasis instead being placed upon illustrating the principles of the invention.

Figure 1A:
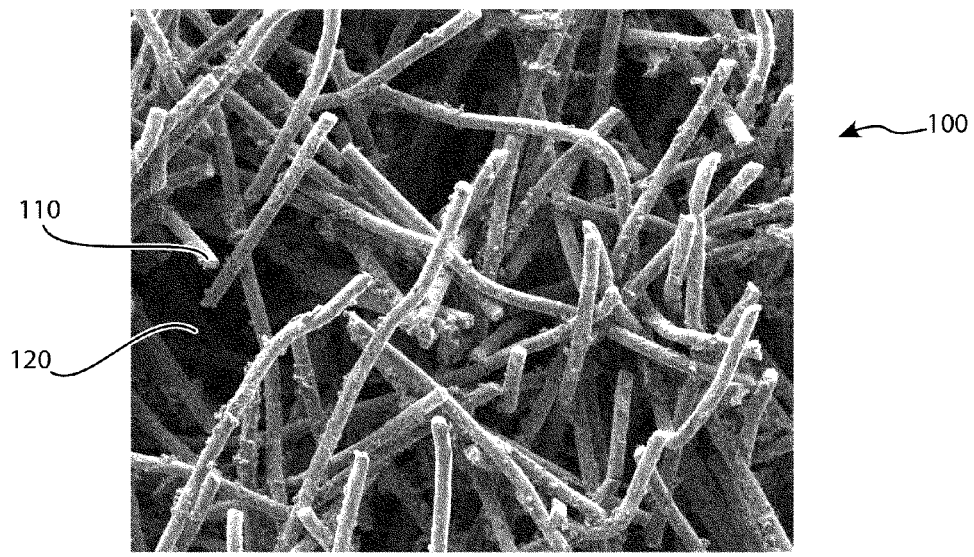
FIG. 1A is an optical micrograph at approximately 50× magnification showing an embodiment of a tissue scaffold according to the present invention.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

The present invention provides a synthetic prosthetic tissue scaffold for the repair of tissue defects. As used herein, the terms "synthetic prosthetic tissue scaffold" and "bone tissue scaffold" and "tissue scaffold" and "synthetic bone prosthetic" in various forms may be used interchangeably throughout. In an embodiment, the synthetic prosthetic tissue scaffold is bioinert once implanted in living tissue. In an embodiment, the synthetic prosthetic tissue scaffold is osteoconductive once implanted in living tissue. In an embodiment, the synthetic prosthetic tissue scaffold is osteostimulative once implanted in living tissue. In an embodiment, the synthetic prosthetic tissue scaffold is load bearing once implanted in living tissue.

Various types of synthetic implants have been developed for tissue engineering applications in an attempt to provide a synthetic prosthetic device that mimics the properties of natural bone tissue and promotes healing and repair of tissue. Bioinert materials of metallic and bio-persistent structures have been developed to provide high strength in a porous structure that promotes the growth of new tissue. These porous materials, however, cannot provide porosity having a pore morphology that is optimized for the in-growth of healthy tissue. A disadvantage of prior art bio-persistent metallic and biocompatible implants is that the high load bearing capability does not transfer to regenerated tissue surrounding the implant. When hard tissue is formed, stress loading results in a stronger tissue but the metallic implant shields the newly formed bone from receiving this stress. Stress shielding of bone tissue therefore results in weak bone tissue which can actually be resorbed by the body, which is an initiator of prosthesis loosening.

Implants into living tissue evoke a biological response dependent upon a number of factors, such as the composition of the implant. Bioinert materials are commonly encapsulated with fibrous tissue to isolate the implant from the host. Metals and most polymers produce this interfacial response, as do nearly inert ceramics, such as alumina or zirconia. If the implant has a porous surface of sufficient pore size and pore size distribution, the living tissue will grow into and bond to the implant as a function of the body's natural healing process. This interfacial bonding can lead to an interface that stabilizes the scaffold or implant in the bony bed and provide stress transfer from the scaffold across the bonded interface into the bone tissue. When loads are applied to the repair, the bone tissue including the regenerated bone tissue is stressed, thus limiting bone tissue resorption due to stress shielding.

The challenge in developing a tissue scaffold using biologically inert materials is to attain load bearing strength with porosity sufficient to promote the growth of bone tissue with an elastic modulus that is similar to the surrounding bone so that stress is transmitted to the new tissue to ensure the formation of healthy bone at the implant site. Conventional bioinert materials prepared into a tissue scaffold with sufficient strength to be load bearing strength do not provide the open and interconnected pores having a desired pore size and pore size distribution to promote the in-growth of healthy tissue, or exhibit an elastic modulus that greatly exceeds that of natural bone resulting in stress shielding.

Fiber-based structures are generally known to provide inherently higher strength to weight ratios, given that the strength of an individual fiber can be significantly greater than powder-based or particle-based materials of the same composition. A fiber can be produced with relatively few discontinuities that contribute to the formation of stress concentrations for failure propagation. By contrast, a powder-based or particle-based material requires the formation of bonds between each of the adjoining particles, with each bond interface potentially creating a stress concentration. Furthermore, a fiber-based structure provides for stress relief and thus, greater strength, when the fiber-based structure is subjected to strain in that the failure of any one individual fiber does not propagate through adjacent fibers. Accordingly, a fiber-based structure exhibits superior mechanical strength properties over an equivalent size and porosity than a powder-based material of the same composition.

The present invention provides a material for tissue engineering applications that is bioinert, with load bearing capability at a low elastic modulus, and osteostimulative with a pore structure that can be controlled and optimized to promote the in-growth of bone.

FIG. 1A is an optical micrograph at approximately 50× magnification showing an embodiment of a tissue scaffold 100 of the present invention. The tissue scaffold 100 is a rigid three-dimensional matrix 110 forming a structure that mimics bone structure in strength, elastic modulus, and pore morphology. As used herein, the term "rigid" means the structure does not significantly yield upon the application of stress until it fractured in the same way that natural bone would be considered to be a rigid structure. The scaffold 100 is a porous material having a network of pores 120 that are generally interconnected. In an embodiment, the interconnected network of pores 120 provide osteoconductivity. As used herein, the term osteoconductive means that the material can facilitate the in-growth of bone tissue. Cancellous bone of a typical human has a compressive crush strength ranging between about 4 to about 12 MPa with an elastic modulus ranging between about 0.1 to about 1.0 GPa. As will be shown herein below, the tissue scaffold 100 of the present invention can provide a porous osteostimulative structure in a tantalum material with porosity greater than 50% and compressive crush strength greater than 4 MPa, up to, and exceeding 110 MPa, with an elastic modulus that closely matches natural bone (e.g., 0.1-3.5 GPa).

In an embodiment, the three dimensional matrix 110 is formed from fibers that are bonded and fused into a rigid structure, with a bioinert composition. The use of fibers as a raw material for creating the three dimensional matrix 110 provides a distinct advantage over the use of conventional powder-based raw materials including materials formed from chemical vapor deposition techniques. In an embodiment, the fiber-based raw material provides a structure that has more strength at a given porosity than a powder-based structure. In an embodiment, the fiber-based raw material provides a structure that has a lower elastic modulus than a conventional structures.

The tissue scaffold 100 of the present invention provides desired mechanical and chemical characteristics, combined with pore morphology to promote osteoconductivity. The network of pores 120 is the natural interconnected porosity resulting from the space between intertangled, nonwoven fiber material in a structure that mimics the structure of natural bone. Furthermore, using methods described herein, the pore size can be controlled, and optimized, to enhance the flow of blood and body fluid within of the scaffold 100 and regenerated bone. For example, pore size and pore size distribution can be controlled through the selection of pore formers and organic binders that are volatilized during the formation of the scaffold 100. Pore size and pore size distribution can be determined by the particle size and particle size distribution of the pore former including a single mode of pore sizes, a bi-modal pore size distribution, and/or a multi-modal pore size distribution. The porosity of the scaffold 100 can be in the range of about 40% to about 85%. In an embodiment, this range promotes the process of osteoinduction of the regenerating tissue once implanted in living tissue while exhibiting load bearing strength.

The scaffold 100 is fabricated using fibers as a raw material. The fibers can be composed of a bioinert material. The term "fiber" as used herein is meant to describe a wire, filament, rod or whisker in a continuous or discontinuous form having an aspect ratio greater than one, and formed from a wire-drawing or fiber-forming process such as drawn, spun, blown, or other similar process typically used in the formation of fibrous materials. Bioinert wires or fibers can be fabricated from a bioinert composition that is capable of being formed into a wire or fiber form, such as bioinert materials such as tantalum, titanium, stainless steel or alloys of such materials, or alumina or other bioinert oxides. Bioinert materials including titanium and titanium alloys, can be formed by conventional metal wire drawing methods, including multiple and/or successive draws to reduce the wire diameter to the desired fiber diameter, and cut or chopped to length. The fibers can be fabricated from precursors of bioinert compositions, that form a bioinert composition upon formation of the three-dimensional matrix 110 while forming the scaffold 100. Bioinert fiber compositions can be used to fabricate a scaffold 100 that is both load bearing and osteoconductive and/or osteostimulative.

Referring still to FIG. 1A, the network of pores 120 within the three-dimensional matrix 110 has a unique structure with properties that are particularly advantageous for the in-growth of bone tissue as a scaffold 100. The characteristics of the pore space 120 can be controlled through the selection of volatile components, as herein described below. Pore size and pore size distribution are important characteristics of the network of pores 120, that can be specified and controlled and thus, predetermined through the selection of volatile components having specific particle sizes and distributions to provide a structure that is osteoconductive, while maintaining strength for load bearing applications. Additionally, the network of pores 120 exhibits improved interconnectivity with large relative throat sizes between the pores due to the position of the fibers from the binder and pore former over the prior art materials that further enhances the osteoconductivity of the tissue scaffold 100 of the present invention. The network of pores 120 arises from the space resulting from the natural packing density of fibrous materials, and the space resulting from displacement of the fibers by volatile components mixed with the fiber during the formation of the scaffold 100. As further described below, the bioinert material forming the three dimensional matrix 110 is fabricated by fusing and bonding overlapping and intertangled fibers.

Figure 1B:
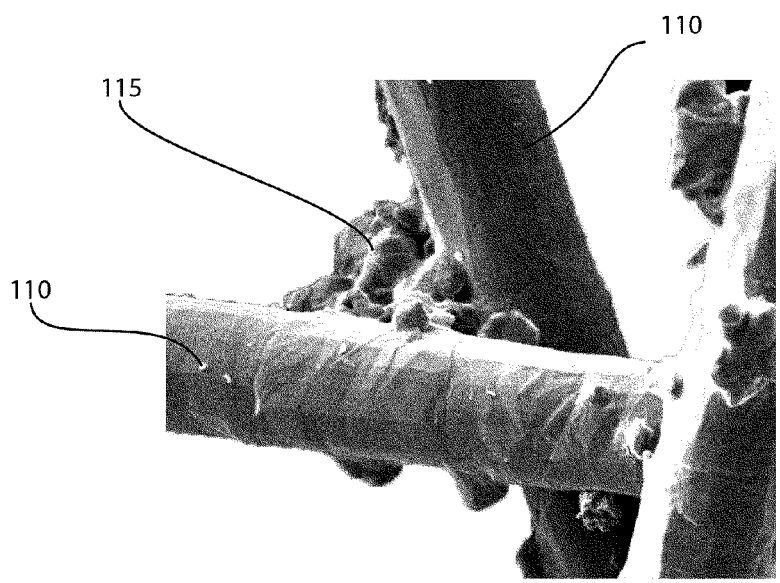
FIG. 1B is an optical micrograph at approximately 500× magnification showing an embodiment of a tissue scaffold according to the present invention.

Referring now to FIG. 1B, an exploded view of bonded and overlapping intertangled fibers is shown in a high magnification view of an embodiment of the present invention. Fibers 110 are fused and bonded to overlapping fibers 110 with a bonding agent 115. The bonding agent 115 can supplement and enhance the fiber-to-fiber bonds that create the three dimensional matrix of the tissue scaffold 100. The fibers and bonding agents are non-volatile components that are prepositioned through the formation of a homogeneous mixture with volatile components, such as binders and pore formers, including, for example, organic materials to predetermine the resulting pore size, pore distribution, and throat size between pores. Furthermore, the volatile components effectively increase the number of pore interconnections by increasing the throat size between pores resulting in pores being connected to multiple pores. Bulk fibers are deagglomerated and distributed throughout the mixture, resulting in a relative positioning of the fibrous materials in an overlapping and intertangled relationship within the volatile organic materials. Upon removal of the volatile components, and fusing and bonding of the fiber to form the three-dimensional matrix 110, the network of pores 120 results from the space occupied by the volatile components.

An objective of the scaffold of the present invention is to facilitate in situ tissue generation as an implant within living tissue. While there are many criteria for an ideal scaffold for bone tissue repair, an important characteristic is a highly interconnected porous network with both pore sizes, and pore interconnections, large enough for cell migration, fluid exchange and eventually tissue in-growth and vascularization (e.g., penetration of blood vessels). The tissue scaffold 100 of the present invention is a porous structure with pore size and pore interconnectivity that is particularly adapted for the in-growth of bone tissue. The network of pores 120 has a pore size that can be controlled through the selection of volatile components used to fabricate the tissue scaffold 100, to provide an average pore size of at least 100 µm. Embodiments of the tissue scaffold 100 have an average pore size in the range of about 50 µm to about 600 µm, and alternatively, an average pore size in the range of about 100 µm to about 500 µm. The volatile components, including organic binder and pore formers, that form the pores, and the intertangled fibers that extend from one pore to at least an adjacent pore, as determined by the predetermined position of the fibers from the volatile components, ensure a high degree of interconnectivity with large pore throat sizes within the three-dimensional matrix. It may be desirable to have a pore size distribution that is bimodal or multi-modal as determined by in vivo analysis. Multimodal pore size distributions can be provided by the selection of pore former materials exhibiting similar multi-modal particle size distributions. Similarly, mixed fiber materials of varying characteristics, such as thickness or diameter, length, or cross-sectional shape can influence the size and size distribution of the pores.

Figure 2:
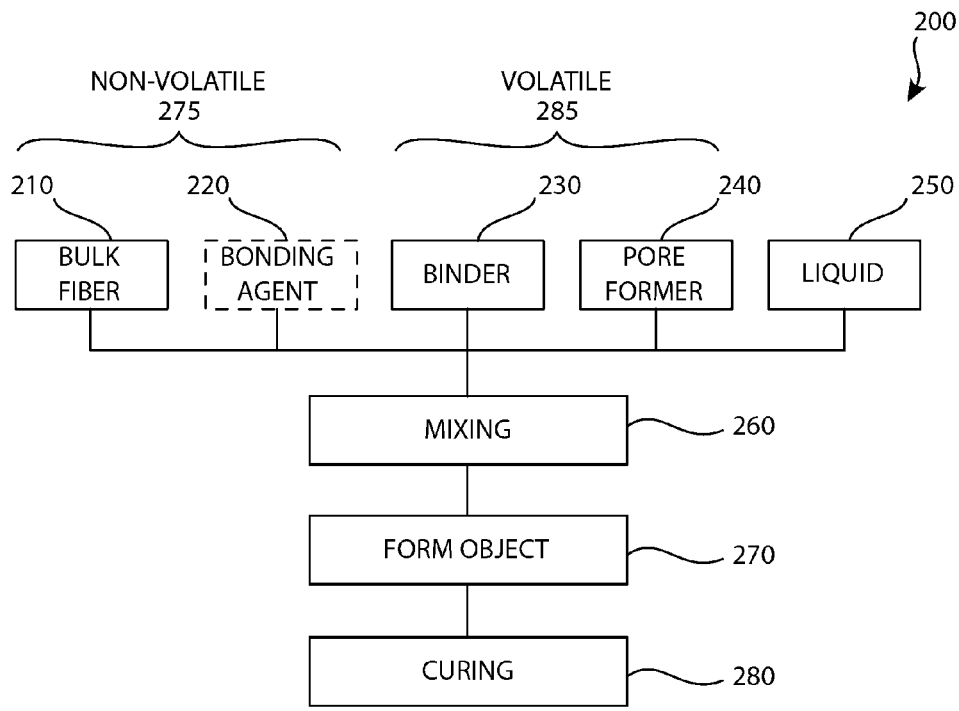
FIG. 2 is a flowchart of an embodiment of a method of the present invention for forming the tissue scaffold of FIG. 1A and FIG. 1B.

Referring to FIG. 2, an embodiment of a method 200 of forming the tissue scaffold 100 is shown. Generally, bulk fibers 210 are mixed with a binder 230 and a liquid 250 to form a plastically moldable material, which is then cured to form the tissue scaffold 100. The curing step 280 selectively removes the volatile elements of the mixture, leaving the pore space 120 open and interconnected, and effectively fuses and bonds the fibers 210 into the rigid three-dimensional matrix 110.

The bulk fibers 210 can be provided in bulk form, or as chopped fibers. The diameter of the fiber 210 can range from about 2 to about 500 μm and typically between about 25 to about 200 μm. Fibers 210 of this type are typically produced with a relatively narrow and controlled distribution of fiber diameters, and fibers of a given diameter may be used, or a mixture of fibers having a range of fiber diameters can be used. The diameter of the fibers 210 will influence the resulting pore size and pore size distribution of the porous structure, as well as the size and thickness of the three-dimensional matrix 110, which will influence not only the osteoconductivity of the scaffold 100, but also the resulting strength characteristics, including compressive strength and elastic modulus. The fibers 210 are typically cut or chopped to length. The fiber length can be in the range of about 3 to about 1000 times the diameter of the fiber, and typically between about 20 to 50 times the diameter of the fiber.

The binder 230 and the liquid 250, when mixed with the fiber 210, create a plastically formable batch mixture that enables the fibers 210 to be evenly distributed throughout the batch, while providing green strength to permit the batch material to be formed into the desired shape in the subsequent forming step 270. An organic binder material can be used as the binder 230, such as methylcellulose, hydroxypropyl methylcellulose (HPMC), ethylcellulose and combinations thereof. The binder 230 can include materials such as polyethylene, polypropylene, polybutene, polystyrene, polyvinyl acetate, polyester, isotactic polypropylene, atactic polypropylene, polysulphone, polyacetal polymers, polymethyl methacrylate, fumaron-indane copolymer, ethylene vinyl acetate copolymer, styrene-butadiene copolymer, acryl rubber, polyvinyl butyral, inomer resin, epoxy resin, nylon, phenol formaldehyde, phenol furfural, paraffin wax, wax emulsions, microcrystalline wax, celluloses, dextrines, chlorinated hydrocarbons, refined alginates, starches, gelatins, lignins, rubbers, acrylics, bitumens, casein, gums, albumins, proteins, glycols, hydroxyethyl cellulose, sodium carboxymethyl cellulose, polyvinyl alcohol, polyvinyl pyrrolidone, polyethylene oxide, polyacrylamides, polyethylerimine, agar, agarose, molasses, dextrines, starch, lignosulfonates, lignin liquor, sodium alginate, gum arabic, xanthan gum, gum tragacanth, gum karaya, locust bean gum, irish moss, scleroglucan, acrylics, and cationic galactomanan, or combinations thereof. Although several binders 230 are listed above, it will be appreciated that other binders may be used. The binder 230 provides the desired rheology of the plastic batch material in order to form a desired object and maintaining the relative position of the fibers 210 in the mixture while the object is formed, while remaining inert with respect to the bioinert materials. The physical properties of the binder 230 will influence the pore size and pore size distribution of the pore space 120 of the scaffold 100. Preferably, the binder 230 is capable of thermal disintegration, or selective dissolution, without impacting the chemical composition of the bioinert components, including the fiber 210.

The fluid 250 is added as needed to attain a desired rheology in the plastic batch material suitable for forming the plastic batch material into the desired object in the subsequent forming step 270. Water is typically used, though solvents of various types can be utilized. Rheological measurements can be made during the mixing step 260 to evaluate the plasticity and cohesive strength of the mixture prior to the forming step 270.

Pore formers 240 can be included in the mixture to enhance the pore space 120 of the scaffold 100. Pore formers are non-reactive materials that occupy volume in the plastic batch material during the mixing step 260 and the forming step 270. When used, the particle size and size distribution of the pore former 240 will influence the resulting pore size and pore size distribution of the pore space 120 of the scaffold 100. Particle sizes can typically range between about 25 μm or less to about 450 μm or more, or alternatively, the particle size for the pore former can be a function of the fibers 210 diameter ranging from about 0.1 to about 100 times the diameter of the fibers 210. The pore former 240 must be readily removable during the curing step 280 without significantly disrupting the relative position of the surrounding fibers 210. In an embodiment of the invention, the pore former 240 can be removed via pyrolysis or thermal degradation, or volatization at elevated temperatures during the curing step 280. For example, microwax emulsions, phenolic resin particles, flour, starch, or carbon particles can be included in the mixture as the pore former 240. Other pore formers 240 can include carbon black, activated carbon, graphite flakes, synthetic graphite, wood flour, modified starch, celluloses, coconut shell husks, latex spheres, bird seeds, saw dust, pyrolyzable polymers, poly (alkyl methacrylate), polymethyl methacrylate, polyethyl methacrylate, poly n-butyl methacrylate, polyethers, poly tetrahydrofuran, poly (1,3-dioxolane), poly (alkalene oxides), polyethylene oxide, polypropylene oxide, methacrylate copolymers, polyisobutylene, polytrimethylene carbonate, poly ethylene oxalate, poly beta-propiolactone, poly delta-valerolactone, polyethylene carbonate, polypropylene carbonate, vinyl toluene/alpha-methylstyrene copolymer, styrene/alpha-methyl styrene copolymers, and olefin-sulfur dioxide copolymers. Pore formers 240 may be generally defined as organic or inorganic, with the organic typically burning off at a lower temperature than the inorganic. Although several pore formers 240 are listed above, it will be appreciated that other pore formers 240 may be used. Pore formers 240 can be, though need not be, fully biocompatible since they are removed from the scaffold 100 during processing.

A bonding agent 220 can be optionally included in the mixture to promote bond formation and the performance of the resulting scaffold 100. The bonding agent 220 can include powder-based material of the same composition as the bulk fiber 210, or it can include powder-based material of a different composition. As will be explained in further detail below, the bonding agent 220 based additives enhance the bonding strength of the intertangled fibers 210 forming the three-dimensional matrix 110 through the formation of bonds between adjacent and intersecting fibers 210. The bonding agent 220 can be bioinert metal, glass, glass-ceramic, ceramic, or precursors thereto. In an embodiment of the present invention, the bonding agent 220 is calcium phosphate. In alternative embodiments, the bonding agent 220 is beta-tricalcium phosphate. In yet another alternative embodiment, the bonding agent 220 is hydroxyapatite.

The relative quantities of the respective materials, including the bulk fiber 210, the binder 230, and the liquid 250 depend on the overall porosity desired in the tissue scaffold 100. For example, to provide a scaffold 100 having approximately 60% porosity, the nonvolatile components 275, such as the fiber 210, would amount to approximately 40% of the mixture by volume. The relative quantity of volatile components 285, such as the binder 230 and the liquid 250 would amount to approximately 60% of the mixture by volume, with the relative quantity of binder to liquid determined by the desired rheology of the mixture. Furthermore, to produce a scaffold 100 having porosity enhance by the pore former 240, the amount of the volatile components 285 is adjusted to include the volatile pore former 240. Similarly, to produce a scaffold 100 having strength enhanced by the bonding agent 220, the amount of the nonvolatile components 275 would be adjusted to include the nonvolatile bonding agent 220. It can be appreciated that the relative quantities of the nonvolatile components 275 and volatile components 285 and the resulting porosity of the scaffold 100 will vary as the material density may vary due to the reaction of the components during the curing step 280. Specific examples are provided herein below.

In the mixing step 260, the fiber 210, the binder 230, the liquid 250, the pore former 240 and/or the bonding agent 220, if included, are mixed into a homogeneous mass of a plastically deformable and uniform mixture. The mixing step 260 may include dry mixing, wet mixing, shear mixing, and kneading, which can be necessary to evenly distribute the material into a homogeneous mass while imparting the requisite shear forces to break up and distribute or de-agglomerate the fibers 210 with the non-fiber materials. The amount of mixing, shearing, and kneading, and duration of such mixing processes depends on the selection of fibers 210 and non-fiber materials, along with the selection of the type of mixing equipment used during the mixing step 260, in order to obtain a uniform and consistent distribution of the materials within the mixture, with the desired rheological properties for forming the object in the subsequent forming step 270. Mixing can be performed using industrial mixing equipment, such as batch mixers, shear mixers, and/or kneaders.

The forming step 270 forms the mixture from the mixing step 260 into the object that will become the tissue scaffold 100. The forming step 270 can include extrusion, rolling, pressure casting, or shaping into nearly any desired form in order to provide a roughly shaped object that can be cured in the curing step 280 to provide the scaffold 100. It can be appreciated that the final dimensions of the scaffold 100 may be different than the formed object at the forming step 270, due to expected shrinkage of the object during the curing step 280, and further machining and final shaping may be necessary to meet specified dimensional requirements. In an exemplary embodiment to provide samples for mechanical and in vitro and in vivo testing, the forming step 270 extrudes the mixture into a cylindrical rod using a piston extruder forcing the mixture through a round die.

Figure 3:
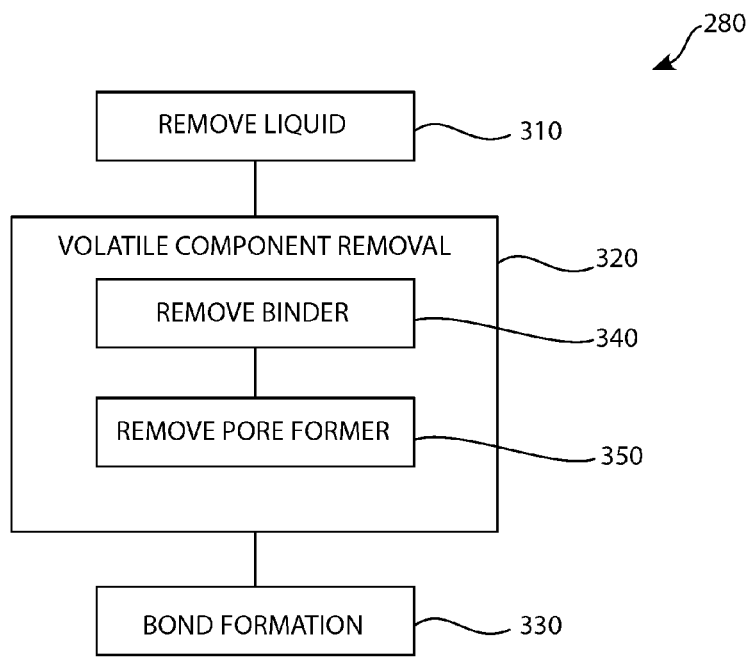
FIG. 3 is a flowchart of an embodiment of a curing step according to the method of FIG. 2 invention.

The object is then cured into the tissue scaffold 100 in the curing step 280, as further described in reference to FIG. 3. In the embodiment shown in FIG. 3, the curing step 280 can be performed as the sequence of three phases: a drying step 310; a volatile component removal step 320; and a bond formation step 330. In the first phase, drying 310, the formed object is dried by removing the liquid using slightly elevated temperature heat with or without forced convection to gradually remove the liquid. Various methods of heating the object can be used, including, but not limited to, heated air convection heating, vacuum freeze drying, solvent extraction, microwave or electromagnetic/radio frequency (RF) drying methods. The liquid within the formed object is preferably not removed too rapidly to avoid drying cracks due to shrinkage. Typically, for aqueous based systems, the formed object can be dried when exposed to temperatures between about 90° C. and about 150° C. for a period of about one hour, though the actual drying time may vary due to the size and shape of the object, with larger, more massive objects taking longer to dry. In the case of microwave or RF energy drying, the liquid itself, and/or other components of the object, adsorb the radiated energy to more evenly generate heat throughout the material. During the drying step 310, depending on the selection of materials used as the volatile components, the binder 230 can congeal or gel to provide greater green strength to provide rigidity and strength in the object for subsequent handling.

Once the object is dried, or substantially free of the liquid component 250 by the drying step 310, the next phase of the curing step 280 proceeds to the volatile component removal step 320. This phase removes the volatile components (e.g., the binder 230 and the pore former 240) from the object leaving only the non-volatile components that form the three-dimensional matrix 110 of the tissue scaffold 100. The volatile components can be removed, for example, through pyrolysis or by thermal degradation, or solvent extraction. The volatile component removal step 320 can be further parsed into a sequence of component removal steps, such as a binder burnout step 340 followed by a pore former removal step 350, when the volatile components 285 are selected such that the volatile component removal step 320 can sequentially remove the components. For example, HPMC used as a binder 230 will thermally decompose at approximately 300° C. A graphite pore former 220 will oxidize into carbon dioxide when heated to approximately 600° C. in the presence of oxygen. Similarly, flour or starch, when used as a pore former 220, will thermally decompose at temperatures between about 300° C. and about 600° C. Accordingly, the formed object composed of a binder 230 of HPMC and a pore former 220 of graphite particles, can be processed in the volatile component removal step 320 by subjecting the object to a two-step firing schedule to remove the binder 230 and then the pore former 220. In this example, the binder burnout step 340 can be performed at a temperature of at least about 300° C. but less than about 600° C. for a period of time. The pore former removal step 350 can then be performed by increasing the temperature to at least about 600° C. with the inclusion of oxygen into the heating chamber. This thermally-sequenced volatile component removal step 320 provides for a controlled removal of the volatile components 285 while maintaining the relative position of the non-volatile components 275 in the formed object.

Figure 4:
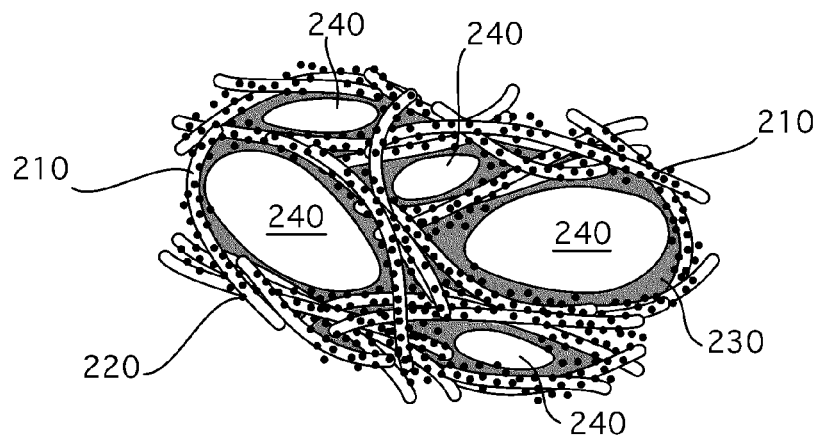
FIG. 4 is a schematic representation of an embodiment of an object fabricated according to a method of the present invention.
Figure 5:
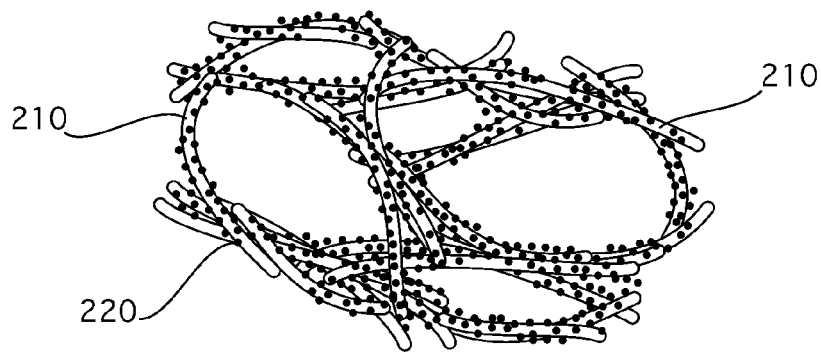
FIG. 5 is a schematic representation of the object of FIG. 4 upon completion of a volatile component removal step of the method of the present invention.

FIG. 4 depicts a schematic representation of the various components of the formed object prior to the volatile component removal step 320. The fibers 210 are intertangled within a mixture of the binder 230 and the pore former 240. Optionally, the bonding agent 220 can be further distributed in the mixture. FIG. 5 depicts a schematic representation of the formed object upon completion of the volatile component removal step 320. The fibers 210 maintain their relative position as determined from the mixture of the fibers 210 with the volatile components 285 as the volatile components 285 are removed. Upon completion of the removal of the volatile components 285, the mechanical strength of the object may be quite fragile, and handling of the object in this state should be performed with care. In an embodiment, each phase of the curing step 280 is performed in the same oven or kiln In an embodiment, a handling tray is provided upon which the object can be processed to minimize handling damage.

Figure 6:
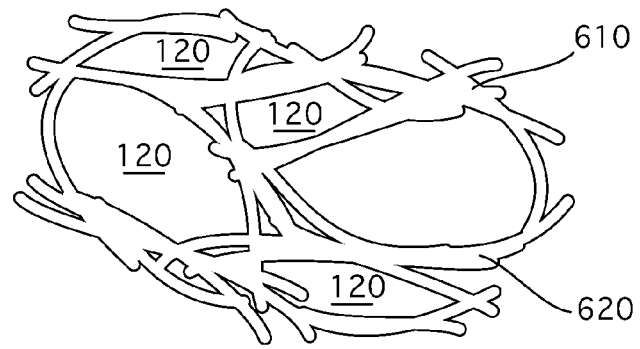
FIG. 6 is a schematic representation of the object of FIG. 5 upon completion of a bond formation step of the method of the present invention.

FIG. 6 depicts a schematic representation of the formed object upon completion of the last step of the curing step 280, bond formation 330. Pore space 120 is created where the binder 230 and the pore former 240 were removed, and the fibers 210 are fused and bonded into the three dimensional matrix 110. The characteristics of the volatile components 285, including the size of the pore former 240 and/or the distribution of particle sizes of the pore former 240 and/or the relative quantity of the binder 230, together cooperate to predetermine the resulting pore size, pore size distribution, and pore interconnectivity of the resulting tissue scaffold 100. The bonding agent 220 and the bonds that form at overlapping nodes 610 and adjacent nodes 620 of the three dimensional matrix 110 provide for structural integrity of the resulting three-dimensional matrix 110.

Referring back to FIG. 3, the bond formation step 330 converts the nonvolatile components 275, including the bulk fiber 210, into the rigid three-dimensional matrix 110 of the tissue scaffold 100 while maintaining the pore space 120 created by the removal of the volatile components 275. The bond formation step 330 heats the non-volatile components 275 in an environment upon which the bulk fibers 210 bond to adjacent and overlapping fibers 210, and for a duration sufficient to form the bonds, without melting the fibers 210, and thereby destroying the relative positioning of the non-volatile components 275. The bond formation environment and duration depends on the chemical composition of the non-volatile components 275, including the bulk fiber 210. For example, if titanium or titanium alloy-based fibers are used as the bulk fiber 210, the bond formation step 330 can be performed in a vacuum furnace at $10^{-3}$ torr and at a temperature of about 1,200° C. If alumina fibers are used as the bulk fiber 210, the bond formation step 330 can be performed in a static or air-purged kiln at atmospheric pressure and at a temperature of about 1,200° C. to about 1,600° C. Other materials that may be used as the bulk fiber 210 can be heated to a temperature upon which solid state mass transfer occurs at the intersecting and overlapping nodes of the fiber structure, or liquid state bonding occurs, depending upon the composition of the non-volatile materials, in an environment that is conducive to the formation of such bonds, including but not limited to environments such as air, nitrogen, argon or other inert gas, and vacuum.

In the bond formation step 330, the formed object is heated to the bond formation temperature resulting in the formation of bonds at overlapping nodes 610 and adjacent nodes 620 of the fiber structure. If a bonding agent 220 is used, the bonds are formed at overlapping nodes 610 and adjacent nodes 620 of the fiber structure through a reaction of the bonding agent 220 in close proximity to the fibers 210, reacting with the fibers 210 to form bonds. In the bond formation step 330, the material of the fibers 210 may participate in a chemical reaction with the bonding agent 220, or the fibers 210 may remain inert with respect to a reaction of the bonding agent 220. Further still, the bulk fibers 210 may be a mixture of fiber compositions, with a portion, or all of the fibers 210 participating in a reaction forming bonds to create the three-dimensional matrix 110.

The duration of the bond formation step 330 depends on the temperature profile during the bond formation step 330, in that the time at the bond formation temperature of the fibers 210 is limited to a relatively short duration so that the relative position of the non-volatile components 275, including the bulk fibers 210, does not significantly change. The pore size, pore size distribution, and interconnectivity between the pores in the formed object are determined by the relative position of the bulk fibers 210 by the volatile components 285. While the volatile components 285 are likely burned out of the formed object by the time the bond formation temperature is attained, the relative positioning of the fibers 210 and non-volatile components 275 are not significantly altered. The formed object will likely undergo slight or minor densification during the bond formation step 330, but the control of pore size and distribution of pore sizes can be maintained, and therefore predetermined by selecting a particle size for the pore former 240 that is slightly oversize or adjusting the relative quantity of the volatile components 285 to account for the expected densification.

The bonds formed between overlapping and adjacent nodes of the intertangled fibers forming the three-dimensional matrix 110 can be sintered bonds having a composition substantially the same as the composition of the bulk fibers 210. The bonds can also be the result of a reaction between the bulk fibers 210 and the bonding agent 220 to form a bonding phase having a composition that is substantially the same, or different than the composition of the bulk fiber 210. Due to the regulatory requirements relating to the approval of materials for use as a medical device or implant, it may be desirable to use approved material compositions as raw materials that are not significantly altered by the device fabrication methods and processes. Alternatively, it may be desirable to use raw materials that are precursors to an approved material composition, that form the desired composition during the device fabrication methods and processes. The present invention provides a tissue scaffold device that can be either fabricated using a variety of medically approved materials, or fabricated into a medically-approved material composition.

The tissue scaffold 100 of the present invention exhibits controlled pore interconnectivity because of the ability to control the pore morphology by specifying characteristics of the non-volatile components 275 and volatile components 285. For example, the fiber length distribution can exhibit a mode that is greater than the pore former diameter to enhance pore interconnectivity in that the fibers exhibiting this mode will extend from one pore to another, with the space between adjacent fibers creating pore interconnectivity. Further, the fiber diameter being less than the pore former particle size can ensure closer packing of pore former particles to provide improved pore interconnectivity.

The mechanical properties of the tissue scaffold 100 can be controlled and adjusted or optimized for a specific application through the manipulation of various parameters in the fabrication method 200 and/or through the manipulation of various parameters and characteristics of the raw materials including the non-volatile components 275 and the volatile components 285. For example, in a load bearing application, the elastic modulus of the tissue scaffold 100 can be optimized and controlled in various ways as described herein.

A tissue scaffold in a load bearing application preferably distributes load evenly over a large area so that stress is continuously transmitted to the surrounding tissue in order to encourage healthy bone formation throughout the interface. The mechanical property of the tissue scaffold that primarily influences the effectiveness of the scaffold in transmitting continuous stress is elastic modulus. When the elastic modulus of the tissue scaffold is closely matched to the elastic modulus of the surrounding tissue, the stress transmitted through the scaffold to the surrounding tissue stimulates the growth of healthy new tissue. If the elastic modulus of the scaffold is relatively greater than the elastic modulus of the surrounding tissue, regenerated tissue that grows into the scaffold is effectively shielded from stress resulting in a disturbing phenomenon known as bone resorption according to Wolff's Law (bone adapting itself to stress reduction by reducing its mass, either by becoming more porous or by getting thinner). If the elastic modulus of the scaffold is excessively less than the elastic modulus of the surrounding tissue stress cannot be effectively transmitted to the surrounding tissue without deformation of the scaffold and exerting excessive stress and strain on newly formed tissue.

The method and apparatus of the present invention permits the fabrication of an ideally matched elastic modulus through the control of various factors for a given material composition. Generally, variation of fiber 210 characteristics, variation of the characteristics of the volatile components 285, variation of the bonding agent 220 characteristics, and control of the environment of the curing step 280 can result in optimization of the resulting strength, porosity and elastic modulus of the scaffold 100.

Fiber characteristics include composition, diameter, length directly impact the strength and flexibility of the scaffold. Compositional influences arise from the inherent physical characteristics of the fiber materials, such as tensile strength and elastic modulus, including factors such as grain boundaries and brittleness of the material. The diameter of the fiber can impact the resulting strength and flexibility of the scaffold in that thicker fibers tend to be stronger and more stiff. Longer fibers can provide increased flexibility. Additionally, the diameter and length of the fiber, individually or collectively, directly influence the natural packing density of the fiber materials. The greater the natural packing density of the fiber, the more fiber-to-fiber connections are possible in the resulting scaffold. When fiber-to-fiber connections are increased, the strength and modulus of the scaffold is generally increased.

The bonding agent 220, when used, can influence the resulting strength and flexibility of the scaffold. The bonding agent 220 can increase the number of fiber-to-fiber connections in the matrix which will increase the resulting strength and change the elastic modulus accordingly. Additionally, the relative quantity of the bonding agent 220 will increase the amount of non-volatile components relative to the volatile components, which will impact the porosity. Generally, high porosity, with all else being the same, will result in reduced strength. The composition of the bonding agent 220 will impact the strength and flexibility of the resulting scaffold in that the inherent physical characteristics, such as tensile and compressive strength and elastic modulus, are imputed to the resulting scaffold. The particle size of the bonding agent 220 can influence the strength and modulus in that larger particles have a tendency to reside at the intersections of fibers, resulting in more material available to bridge adjacent fibers and joint them into the bonded matrix. Smaller particles have a tendency to remain in the same relative position when the binder is burned out so that it adheres to the surface of the fiber to alter the chemical and physical properties of the fiber. Additionally, the smaller particles and/or smaller relative quantities of the bonding agent 220 may result in fewer fiber-to-fiber bonds, which will reduce the strength and reduce the elastic modulus of the resulting scaffold.

Volatile component characteristics can influence the resulting strength and flexibility of the scaffold. Pore formers can control the size and distribution of the interconnecting pores throughout the scaffold, as described in more detail above. With respect to the influence on mechanical properties of the scaffold 100, an increase in the amount of volatile components, including increased relative quantities of pore former, can impact the strength and lower the elastic modulus of the scaffold, with all else remaining the same. Furthermore, there are secondary interactions with the variables associated with fiber diameter and fiber length with regard to the natural packing density of the fiber material. The volatile components, when mixed with the non-volatile components, can increase bundling of the fibers in that two or more fiber lengths will align substantially adjacent to additional fibers, and bond together along the fiber length, effectively increasing the cross-sectional area of the "struts" that form the matrix of the scaffold. Regions of bundled fiber in this manner will effectively impact the strength and elastic modulus of the scaffold 100.

Processing parameters selected during the method 200 of forming the scaffold 100 can influence the mechanical properties of the scaffold. For example, the curing step 280 environment parameters include heating rate, heating temperature, curing time, and heating environment, such as vacuum, inert gas (nitrogen, argon, etc.), forming gas (reducing environment) or air. Each or combinations of each can influence the number and relative strength of fiber-to-fiber bonds throughout the scaffold.

Additional factors for controlling and optimizing the porosity/strength relationship and the elastic modulus of the scaffold 100 include specific characteristics of the raw materials combined with the certain fabrication process 200 steps that can influence a general alignment of the fibers. The mixing step 260 and the forming step 270 can be adapted to provide a formed object that aligns the fibers substantially in one direction. For example, the use of an extrusion process in the forming step 270 can impart a general alignment of the fibers of the mixture in the direction of extrusion. The physical characteristics of the resulting scaffold 100 can exhibit an elastic modulus that is a function of the orientation of the device, in that the compressive strength and elastic modulus can be relatively high in the extrusion direction, while lower in the direction perpendicular to the extrusion direction. A spinal implant that is used to fuse vertebrae can be designed with these variable characteristics to optimize the load bearing and weight sharing features of the scaffold to ensure the growth of healthy tissue. Fiber orientation may be desirable in certain applications where vascularization into the scaffold is necessary. The oriented fibers will induce pore morphology that exhibits a preferential direction parallel to the fibers. In an application where the scaffold 100 is to fuse bone tissue, the vascularization link between the adjoining bones can be effectively bridged by the scaffold of the present invention.

Furthermore, variations of any one or variations in any combination of the above parameters can be made to attain an optimized or desired strength and elastic modulus, porosity, and pore size distribution for an intended application. Furthermore, the strength, elastic modulus, porosity and pore size distribution, and other mechanical and physical properties can be adjusted for other applications, non-limiting examples of which are herein described.

Figure 7:
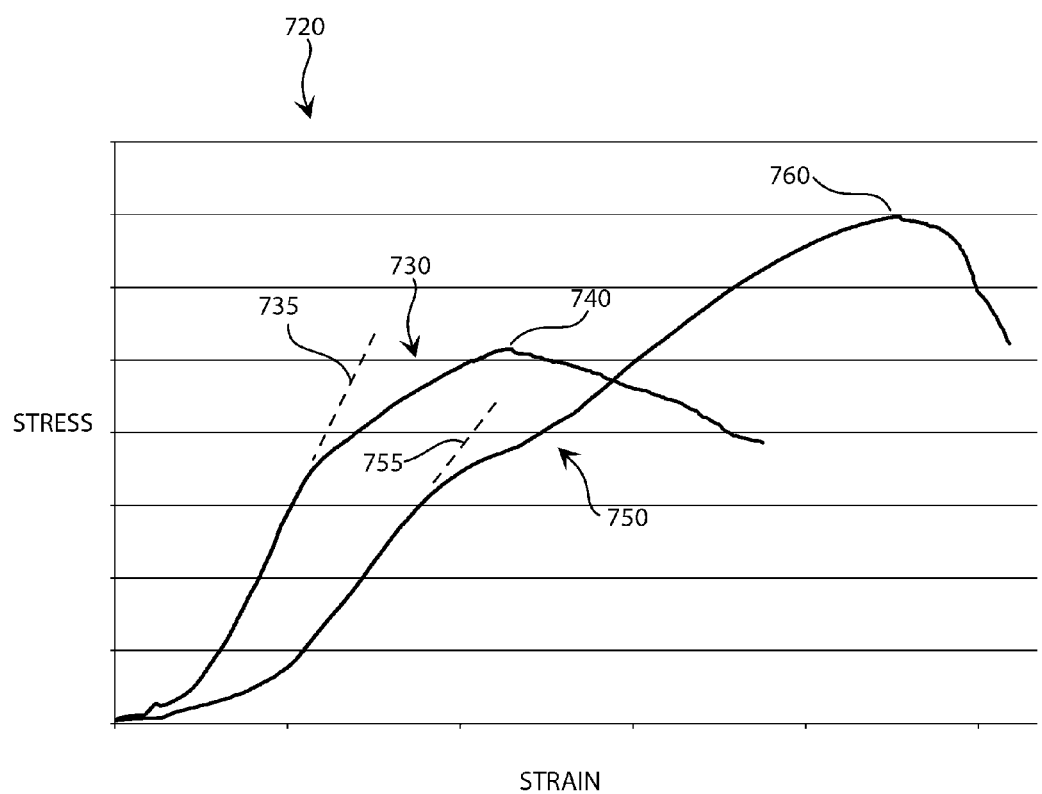
FIG. 7 is a graphic representation of the evaluation of the stress-strain relationship of two exemplary embodiments of the present invention.

FIG. 7 depicts the stress-strain curves 720 resulting from a compression test of two exemplary scaffolds according to the present invention that demonstrates the effect of change in strength and elastic modulus of a scaffold through the addition of a bonding agent during fabrication. Both samples were fabricated in the method 200 described herein above using titanium 6A14V alloy fiber having an average diameter of approximately 63 μm. The first sample was fabricated by mixing 3 grams of fiber cut to 0.045" length with 1 gram of fiber cut to 0.010" length with 0.25 grams HPMC as an organic binder and 1 gram of PMMA with a particle size of about 100 μm as a pore former and approximately 1.5 rams of deinoized water, adjusted as necessary to provide a plastically formable mixture. The mixture was extruded into a 10 mm diameter rod and dried in a convention oven. The volatile components were burned out and then the scaffold was heat treated at 1,400° C. at 0.3 torr vacuum for two hours to create a scaffold having a porosity of 70%. The second sample was fabricated in an identical manner with the only change being an addition of 0.25 grams titanium powder with a particle size of less than 325 μm as a bonding agent 220, with the resulting porosity of 67%. Referring to FIG. 7, the stress-strain curve for the first sample 730 (no bonding agent) exhibits a first elastic modulus 735 and a first peak strength value 740. The second sample 750 (with bonding agent) exhibits a second elastic modulus 755 that is approximately 65% less than the first elastic modulus 735 and a second peak strength value 760 that is approximately 34% greater than the first strength value 740.

Figure 8:
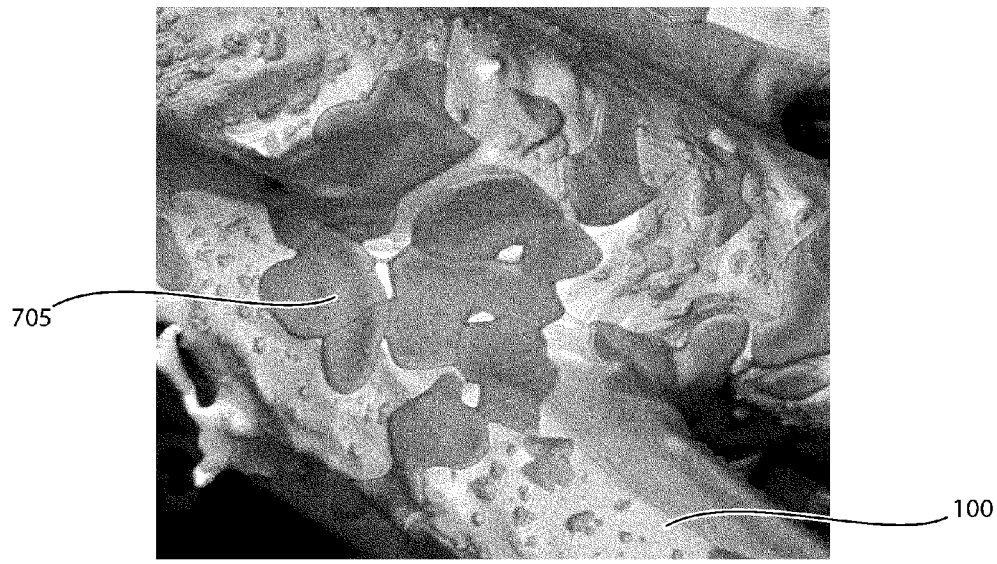
FIG. 8 is an optical micrograph showing an embodiment of a tissue scaffold having a functional material according to the present invention.
Figure 9:
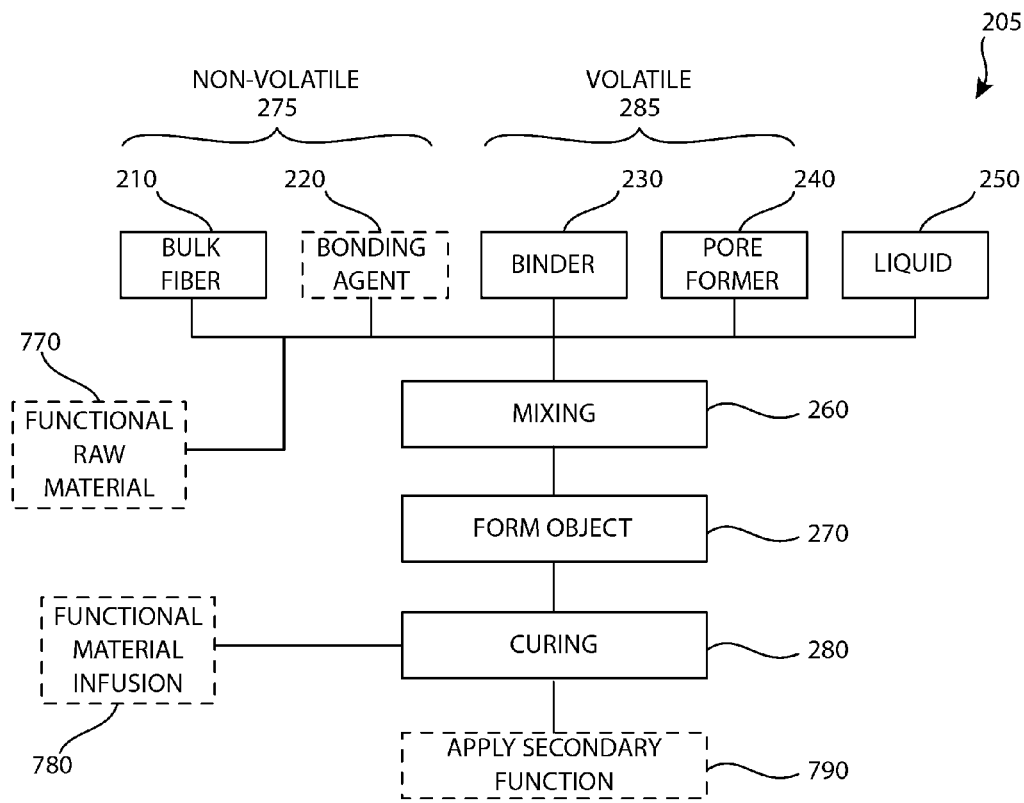
FIG. 9 is a flowchart of an alternate embodiment of a method of the present invention for forming the tissue scaffold of FIG. 8.

FIG. 8 depicts an alternate embodiment of the invention showing the scaffold 100 with a functional material 705 selectively deposited throughout the surface of the scaffold 100. The functional material 705 is selectively deposited to provide secondary functions in the scaffold, such as enhancement of the osteoconductivity and vascularity of the scaffold 100, to prevent the activation of pathological processes during or after implant deployment, to provide therapeutic agents including without limitation antibiotics, anticoagulants, antifungal agents, anti-inflammatory agents, and immunosuppressive agents, to provide radioactive materials that may serve the function of a tracer for detection and location of the implant and/or other functional enhancements. FIG. 9 depicts a method 205 to fabricate the porous scaffold 100 with enhancements to provide secondary functions in the scaffold. The method 205 is generally similar to the method 200 described above with reference to FIG. 2 with the following optional changes. In an embodiment, the functional material 705 can be a material added as a functional raw material 770 as a non-volatile component 275 that is mixed with the fiber 210, and optionally, the bonding agent 220, with the volatile components 285 including the binder 230, the pore former 240, and the liquid 250. The mixture is mixed to distribute the materials including the functional material 705 that is distributed throughout the homogeneous mixture. The homogeneous mixture is then formed into an object 270 and cured into the porous scaffold at step 280, as described above with reference to FIG. 2 and FIG. 3. In this embodiment, the curing step forms fiber-to-fiber bonds and adheres the functional material to the resulting scaffold 100. In a second embodiment, the functional material 705 is added during the curing step, as shown as optional functional material infusion step 780. In this way, the functional material is infused into the scaffold during the bond formation step 330 (as described above with reference to FIG. 3). This can be performed by vapor or plasma deposition in a controlled high temperature environment, such as in a vacuum furnace heat treatment operation. In a third embodiment, the functional material 705 is added during a subsequent coating step 790 that is performed subsequent to the formation of the scaffold 100. In this embodiment, the functional material can be deposited by immersion of the scaffold in a solution containing the functional material 705, chemical vapor deposition of the functional material, cathodic arc deposition of the functional material, or other similar method for deposition of materials. In yet another embodiment, the functional material can be applied in any combination of the optional functional raw material step 770, the optional functional material infusion step 780 and the subsequent coating step 790.

The tissue scaffolds of the present invention can be used in procedures such as an osteotomy (for example in the hip, knee, hand and jaw), a repair of a structural failure of a spine (for example, an intervertebral prosthesis, lamina prosthesis, sacrum prosthesis, vertebral body prosthesis and facet prosthesis), a bone defect filler, fracture revision surgery, tumor resection surgery, hip and knee prostheses, bone augmentation, dental extractions, long bone arthrodesis, ankle and foot arthrodesis, including subtalar implants, and fixation screws pins. The tissue scaffolds of the present invention can be used in the long bones, including, but not limited to, the ribs, the clavicle, the femur, tibia, and fibula of the leg, the humerus, radius, and ulna of the arm, metacarpals and metatarsals of the hands and feet, and the phalanges of the fingers and toes. The tissue scaffolds of the present invention can be used in the short bones, including, but not limited to, the carpals and tarsals, the patella, together with the other sesamoid bones. The tissue scaffolds of the present invention can be used in the other bones, including, but not limited to, the cranium, mandible, sternum, the vertebrae and the sacrum. In an embodiment, the tissue scaffolds of the present invention have high load bearing capabilities compared to conventional devices. In an embodiment, the tissue scaffolds of the present invention require less implanted material compared to conventional devices. Furthermore, the use of the tissue scaffold of the present invention requires less ancillary fixation due to the strength of the material. In this way, the surgical procedures for implanting the device are less invasive, more easily performed, and do not require subsequent surgical procedures to remove instruments and ancillary fixations.

Figure 10:
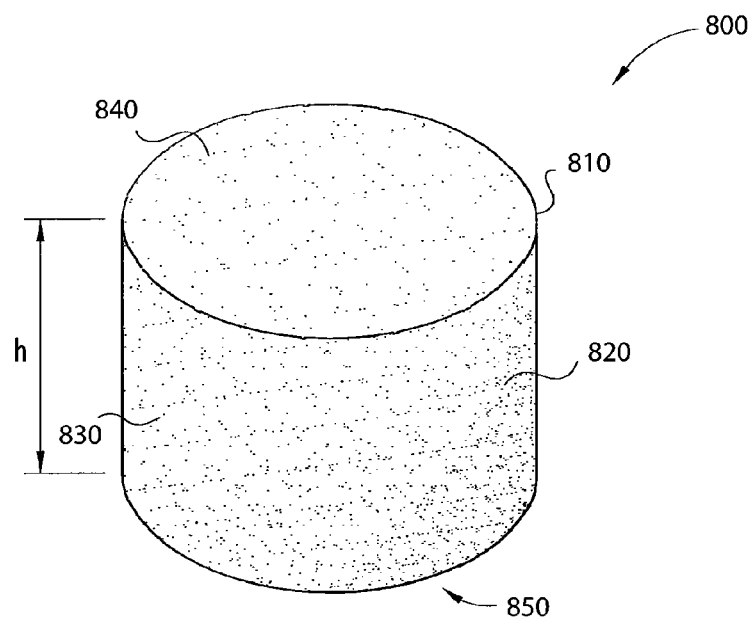
FIG. 10 is a side elevation view of a tissue scaffold according to the present invention manufactured into a spinal implant.
Figure 11:
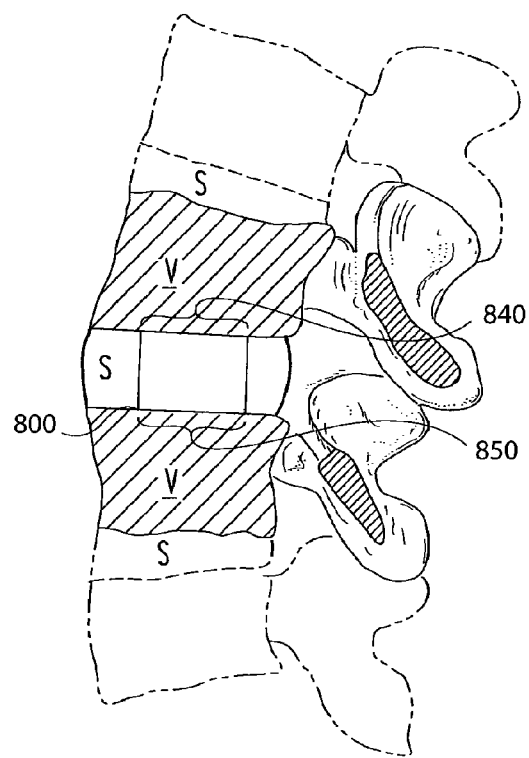
FIG. 11 is a side perspective view of a portion of a spine having the spinal implant of FIG. 10 implanted in the intervertebral space.

In one specific application, a tissue scaffold of the present invention, fabricated as described above, can be used as a spinal implant 800 as depicted in FIG. 10 and FIG. 11. Referring to FIG. 10 and FIG. 11, the spinal implant 800 includes a body 810 having a wall 820 sized for engagement within a space S between adjacent vertebrae V to maintain the space S. The device 800 is formed from bioinert fibers that can be formed into the desired shape using extrusion methods to form a cylindrical shape that can be cut or machined into the desired size. The wall 820 has a height h that corresponds to the height H of the space S. In one embodiment, the height h of the wall 820 is slightly larger than the height H of the intervertebral space S. The wall 820 is adjacent to and between a superior engaging surface 840 and an inferior engaging surface 850 that are configured for engaging the adjacent vertebrae V as shown in FIG. 11.

Figure 12:
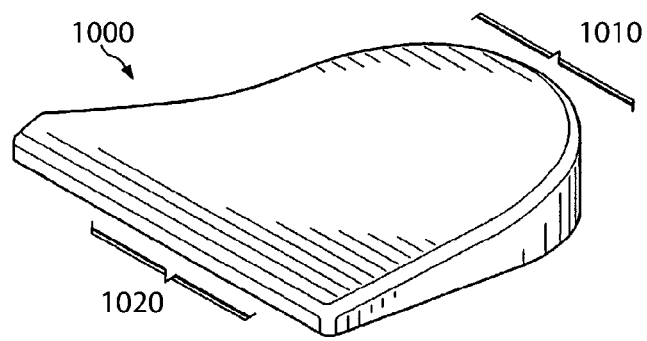
FIG. 12 is a schematic drawing showing an isometric view of a tissue scaffold according to the present invention manufactured into an osteotomy wedge.
Figure 13:
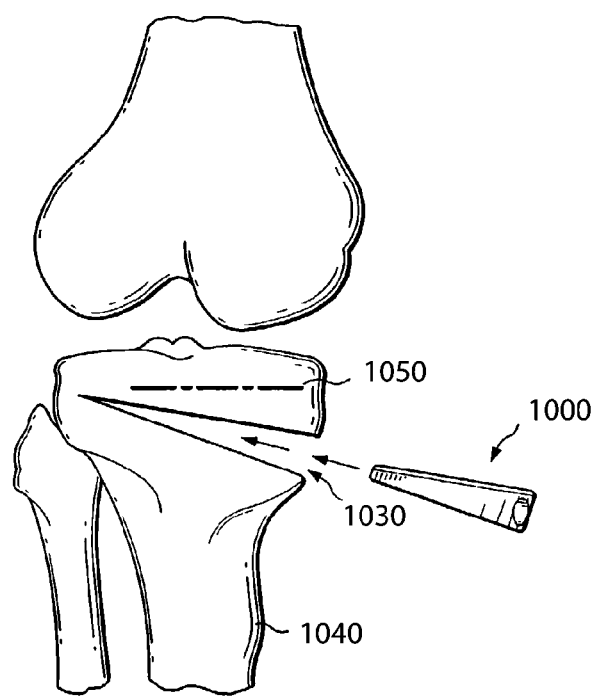
FIG. 13 is a schematic drawing showing an exploded view of the osteotomy wedge of FIG. 12 operable to be inserted into an osteotomy opening in a bone.

In another specific application, a tissue scaffold of the present invention, fabricated as described above, can be used as an osteotomy wedge implant 1000 as depicted in FIGS. 12 and 13. Referring to FIG. 12 and FIG. 13, the osteotomy implant 1000 may be generally described as a wedge designed to conform to an anatomical cross section of, for example, a tibia, thereby providing mechanical support to a substantial portion of a tibial surface. The osteotomy implant is formed from bioinert fibers bonded and fused into a porous material that can be formed from an extruded rectangular block, and cut or machined into the contoured wedge shape in the desired size. The proximal aspect 1010 of the implant 1000 is characterized by a curvilinear contour. The distal aspect 1020 conforms to the shape of a tibial bone in its implanted location. The thickness of the implant 1000 may vary from about five millimeters to about twenty millimeters depending on the patient size and degree of deformity. Degree of angulation between the superior and inferior surfaces of the wedge may also be varied.

FIG. 13 illustrates one method for the use of the osteotomy wedge implant 1000 for realigning an abnormally angulated knee. A transverse incision is made into a medial aspect of a tibia while leaving a lateral portion of the tibia intact and aligning the upper portion 1050 and the lower portion 1040 of the tibia at a predetermined angle to create a space 1030. The substantially wedge-shaped implant 1000 is inserted in the space 1030 to stabilize portions of the tibia as it heals into the desired position with bone regenerating and growing into the implant 1000 as herein described. Fixation pins may be applied as necessary to stabilize the tibia as the bone regenerates and heals the site of the implant.

Generally, the use of a bone tissue scaffold of the present invention as a bone graft involves surgical procedures that are similar to the use of autograft or allograft bone grafts. The bone graft can often be performed as a single procedure if enough material is used to fill and stabilize the implant site. In an embodiment, fixation pins can be inserted into the surrounding natural bone, and/or into and through the bone tissue scaffold. The bone tissue scaffold is inserted into the site and fixed into position. The area is then closed up and after a certain healing and maturing period, the bone will regenerate and become solidly fused to and within the implant.

The use of a bone tissue scaffold of the present invention as a bone defect filler involves surgical procedures that can be performed as a single procedure, or multiple procedures in stages or phases of repair. In an embodiment, a tissue scaffold of the present invention is placed at the bone defect site, and attached to the bone using fixation pins or screws. Alternatively, the tissue scaffold can be externally secured into place using braces. The area is then closed up and after a certain healing and maturing period, the bone will regenerate to repair the defect.

A method of filling a defect in a bone includes filling a space in the bone with a tissue scaffold comprising bioinert fibers bonded into a porous matrix, the porous matrix having a pore size distribution to facilitate in-growth of bone tissue; and attaching the tissue scaffold to the bone.

A method of treating an osteotomy includes filling a space in the bone with a tissue scaffold comprising bioinert fibers bonded into a porous matrix, the porous matrix having a pore size distribution to facilitate in-growth of bone tissue; and attaching the tissue scaffold to the bone.

A method of treating a structural failure of a vertebrae includes filling a space in the bone with a tissue scaffold comprising bioinert fibers bonded into a porous matrix, the porous matrix having a pore size distribution to facilitate in-growth of bone tissue; and attaching the tissue scaffold to the bone.

A method of fabricating a synthetic bone prosthesis includes mixing fiber with a binder, a pore former and a liquid to provide a plastically formable batch; kneading the formable batch to distribute the fiber with the pore former and the binder, the formable batch a homogeneous mass of intertangled and overlapping fiber; forming the formable batch into a desired shape to provide a shaped form; drying the shaped form to remove the liquid; heating the shaped form to remove the binder and the pore former; and heating the shaped form to a bond formation temperature using a primary heat source and a secondary heat source to form bonds between the intertangled and overlapping bioinert fiber.

In an embodiment, the present invention discloses use of bioinert fibers bonded into a porous matrix, the porous matrix having a pore size distribution to facilitate in-growth of bone tissue for the treatment of a bone defect.

In an embodiment, the present invention discloses use of bioinert fibers bonded into a porous matrix, the porous matrix having a pore size distribution to facilitate in-growth of bone tissue for the treatment of an osteotomy.

In an embodiment, the present invention discloses use of bioinert fibers bonded into a porous matrix, the porous matrix having a pore size distribution to facilitate in-growth of bone tissue for the treatment of a structural failure of various parts of a spinal column.

Examples

The following examples are provided to further illustrate and to facilitate the understanding of the disclosure. These specific examples are intended to be illustrative of the disclosure and are not intended to be limiting in an way.

In a first exemplary embodiment a scaffold is formed from titanium fiber by mixing 4 grams of titanium 6A14V alloy fiber having an average diameter of approximately 225 µm chopped into lengths of approximately 1 to 3 mm, in bulk form, as the non-volatile components with 0.125 gram of HPMC as an organic binder and 0.5 grams of PMMA with a particle size of 25-30 µm as a pore former and approximately 1.5 grams of deionized water, adjusted as necessary to provide a plastically formable mixture. The mixture was extruded into a 10 mm diameter rod and dried in a convection oven. The volatile components were burned out and then heat treated at 1,400° C. at 0.3 torr vacuum for two hours. The porosity for this example was measured to be 69.1%.

In a second exemplary embodiment a scaffold is formed from alumina fiber by mixing 50 grams of alumina fiber having an average diameter of approximately 3-5 microns with 30 grams hydroxyapatite powder and 0.8 grams magnesium carbonate powder as the non-volatile components with 65 grams graphite powder having a mean particle size of 45 microns (Asbury Carbon A625 graphite) as the pore former with 5 grams HPMC as the binder and 70 grams of deionized water, adjusted as necessary to provide a plastically formable mixture. The mixture was extruded into a 10 mm diameter rod and dried in a convection oven. The volatile components were burned out in an air-purged oven and then heat treated at 1,600° C. at atmospheric pressure, static air kiln for two hours. The resulting composition of the scaffold is alumina fiber bonded with a hydroxyapatite ceramic bonded porous structure, and the porosity for this example was measured to be 68%.

In a third exemplary embodiment a scaffold is formed from alumina fiber by mixing 50 grams of alumina fiber having an average diameter of approximately 3-5 microns with 50 grams hydroxyapatite powder and 0.8 grams magnesium carbonate powder as the non-volatile components with 65 grams graphite powder having a mean particle size of 250 microns (Asbury Carbon 4015 graphite) as the pore former with 5 grams HPMC as the binder and 70 grams of deionized water, adjusted as necessary to provide a plastically formable mixture. The mixture was extruded into a 10 mm diameter rod and dried in a convection oven. The volatile components were burned out in an air-purged oven and then heat treated at 1,400° C. at atmospheric pressure, static air kiln for two hours. The resulting composition of the scaffold is alumina fiber bonded with a hydroxyapatite ceramic bonded porous structure, and the porosity for this example was measured to be 68%.

In a fourth exemplary embodiment a scaffold is formed from magnesium aluminosilicate fiber by mixing 50 grams of ISOFRAX fiber from Unifrax LLC, Niagara Falls, N.Y., having an average diameter of approximately 10 microns with 30 grams hydroxyapatite powder as the non-volatile components with 65 grams graphite powder having a mean particle size of 250 microns (Asbury Carbon 4015 graphite) as the pore former with 5 grams HPMC as the binder and 80 grams of deionized water, adjusted as necessary to provide a plastically formable mixture. The mixture was extruded into a 10 mm diameter rod and dried in a convection oven. The volatile components were burned out in an air-purged oven and then heat treated at 1,200° C. at atmospheric pressure, static air kiln for two hours. The resulting composition of the scaffold is magnesium aluminosilicate fiber bonded with a hydroxyapatite ceramic bonded porous structure, and the porosity for this example was measured to be 69%.

In a fifth exemplary embodiment a scaffold is formed from titanium fiber by mixing 0.9 grams of pure titanium fiber having an average diameter of approximately 225 µm chopped into lengths of approximately 1 to 3 mm, in bulk form, as the non-volatile components with 0.3 grams of HPMC as an organic binder and 0.5 grams of potato starch with a particle size of approximately 50 μm as a pore former and approximately 2 grams of deionized water, adjusted as necessary to provide a plastically formable mixture. The mixture was extruded into a 10 mm diameter rod and dried in a convection oven. The volatile components were burned out and then heat treated at 1,400° C. at 0.3 torr vacuum for two hours. The porosity for this example was measured to be 69.1%.

In a sixth exemplary embodiment a scaffold is formed from titanium fiber by mixing 2 grams of titanium 6A14V alloy fiber having an average diameter of approximately 65 μm chopped into lengths of approximately 1-2 mm, in bulk form, and 0.5 grams of titanium 6A14V alloy powder as the bonding agent having a particle size of less than 44 μm (−325 mesh) as the non-volatile components with 0.5 grams of HPMC as an organic binder and 0.5 grams of polyethylene particles having a particle size of approximately 150 μm as a pore former and approximately 2 grams of deionized water, adjusted as necessary to provide a plastically formable mixture. The mixture was extruded into a 10 mm diameter rod and dried in a convection oven. The volatile components were burned out at 350° C. for 14 hours and then heat treated at 1,400° C. using a ramp rate of 5° C. per minute in an argon-purged kiln holding at 1,400° C. for two hours. The porosity for this example was measured to be 88.1%.

In a seventh exemplary embodiment a scaffold is formed from a mixture of two types of titanium fiber. In this example, 2 grams of titanium 6A14V alloy fiber having an average diameter of approximately 65 μm chopped into lengths of approximately 1-2 mm were mixed with 2 grams of titanium 6A14V alloy fiber having an average diameter of approximately 225 μm chopped into lengths of approximately 1-3 mm and 1.0 grams of titanium 6A14V alloy powder as the bonding agent having a particle size of less than 44 μm (−325 mesh) as the non-volatile components with 0.5 grams of HPMC as an organic binder and 0.5 grams of polyethylene particles having a particle size of approximately 150 μm as a pore former and approximately 2 grams of deionized water, adjusted as necessary to provide a plastically formable mixture. The mixture was extruded into a 10 mm diameter rod and dried in a convection oven. The volatile components were burned out at 350° C. for 14 hours and then heat treated at 1,400° C. using a ramp rate of 5° C. per minute in an argon-purged kiln holding at 1,400° C. for two hours.

The present invention has been herein described in detail with respect to certain illustrative and specific embodiments thereof, and it should not be considered limited to such, as numerous modifications are possible without departing from the spirit and scope of the appended claims.

What is claimed is:

1. A method of fabricating a porous orthopedic implant comprising:
    providing bulk fiber;
    providing a bonding agent;
    mixing the bulk fiber and the bonding agent with volatile materials including a binder, a pore former, and a liquid to provide a batch material;
    forming the batch material into a shaped object; and
    curing shaped object by removing the volatile materials and bonding the bulk fiber using the bonding agent to provide the orthopedic implant;
    wherein a raw material characteristic is selected to provide an elastic modulus of the orthopedic implant that is the same as natural bone with a compressive strength that exceeds 4 MPa and a porosity greater than 50%.

2. The method according to claim 1 wherein the raw material characteristic is a packing density of the bulk fiber that is selected by controlling the length of the bulk fiber.

3. The method according to claim 1 wherein the raw material characteristic is a packing density of the bulk fiber that is selected by controlling the diameter of the bulk fiber.

4. The method according to claim 1 wherein the raw material characteristic is a packing density of the bulk fiber that is selected by controlling the diameter and the length of the bulk fiber.

5. The method according to claim 1 wherein the raw material characteristic is a relative quantity of the bulk fiber to the bonding agent that is selected by reducing the amount of the bonding agent.

6. The method according to claim 1 wherein the raw material characteristic is a particle size of the bonding agent.

7. The method according to claim 6 wherein the raw material characteristic is selected by reducing the particle size of the bonding agent.

8. The method according to claim 1 wherein the raw material characteristic is the particle size of the pore former.

9. The method according to claim 8 wherein the raw material characteristic is selected by reducing the particle size of the pore former.

10. The method according to claim 8 wherein the raw material characteristic is the composition of the bonding agent.

11. The method according to claim 10 wherein the composition of the bonding agent is glass.

12. The method according to claim 11 wherein the bulk fiber is glass.

* * * * *